United States Patent [19]

Wand

[11] Patent Number: 5,933,936
[45] Date of Patent: Aug. 10, 1999

[54] SYRINGE NEEDLE SAFETY VISE AND ASSOCIATED DISINFECTING APPARATUS

[76] Inventor: Joseph S. Wand, 3715 Nielsen Rd., Santa Rosa, Calif. 95404-1723

[21] Appl. No.: 08/970,786

[22] Filed: Nov. 14, 1997

Related U.S. Application Data

[60] Provisional application No. 60/031,111, Nov. 14, 1996.

[51] Int. Cl.$^6$ ..................................................... B23Q 1/00
[52] U.S. Cl. ........................... 29/283; 29/240; 29/240.5; 29/239; 422/301; 422/302; 422/303
[58] Field of Search .......................... 29/240, 283, 240.5, 29/239; 422/301, 302, 303

[56] References Cited

U.S. PATENT DOCUMENTS

| | | |
|---|---|---|
| 4,380,292 | 4/1983 | Cramer . |
| 4,862,573 | 9/1989 | Kelson et al. ............... 29/240 |
| 4,938,514 | 7/1990 | D'Addezio . |
| 4,989,307 | 2/1991 | Sharpe et al. . |
| 5,168,612 | 12/1992 | Schultz et al. . |
| 5,184,721 | 2/1993 | Wengyn et al. .......... 422/301 |
| 5,212,362 | 5/1993 | Burden et al. . |
| 5,368,576 | 11/1994 | Brown et al. . |
| 5,383,862 | 1/1995 | Berndt et al. . |
| 5,424,047 | 6/1995 | Zwingenberger ........ 422/302 |
| 5,427,234 | 6/1995 | Upchurch . |
| 5,472,433 | 12/1995 | Suzuki . |

*Primary Examiner*—David A. Scherbel
*Assistant Examiner*—Daniel Shanley
*Attorney, Agent, or Firm*—Richard C. Litman

[57] ABSTRACT

A safety vise for collection and disposal of used hypodermic needles, having an associated disinfecting apparatus which is operably coupled to a viseing mechanism to prevent its subsequent use unless a disinfecting operation using the disinfecting apparatus is performed. The safety vise is primarily intended for reclaiming the sleeve of a pistonless blood collection system, like VACUTAINER® assemblies, assembled from three independent sections: a sleeve, a specimen tube, and a double-ended needle. A disposable, needle collection container seats a project top. The project top includes a first station having guard elements particularly structured for safely removing a double-ended needle, and a second station for disinfecting the sleeve. The viseing mechanism is internally affixed to the project top and operably links the first station to the second station so that, after a needle and syringe is initially introduced into the first station and the viseing mechanism is used to remove the needle in a one handed technique, the viseing mechanism is rendered subsequently inoperable unless the needle is disengaged from the viseing mechanism by operation of disinfecting the sleeve at the second station. The viseing mechanism may comprise elongated, bipartite jaw members which are separable by a downward pressure on the disinfecting apparatus during cleaning, wherein a wedge component is driven between jaw members causing the separation and loosening of the jaws holding the used needle, allowing the used needle to fall into the collection container.

15 Claims, 8 Drawing Sheets

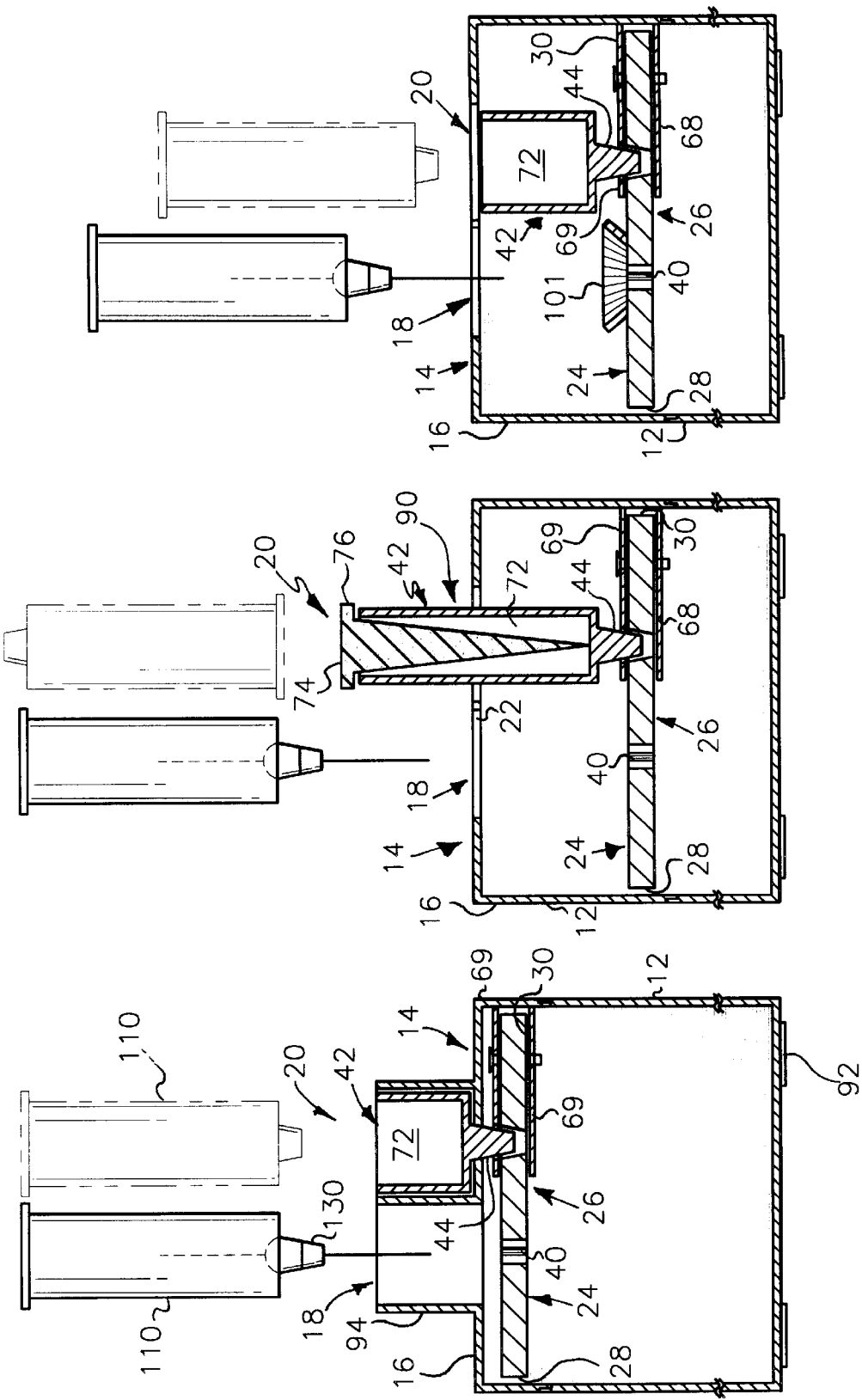

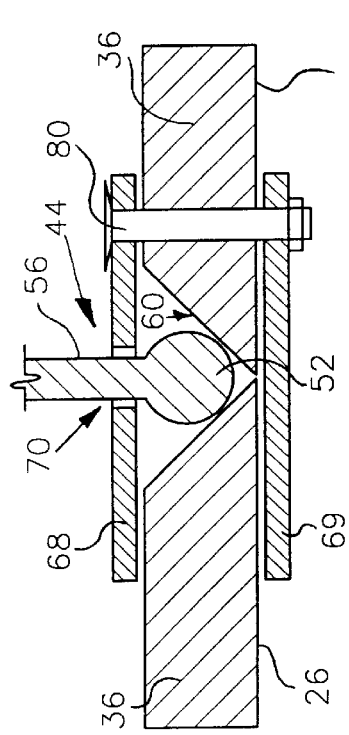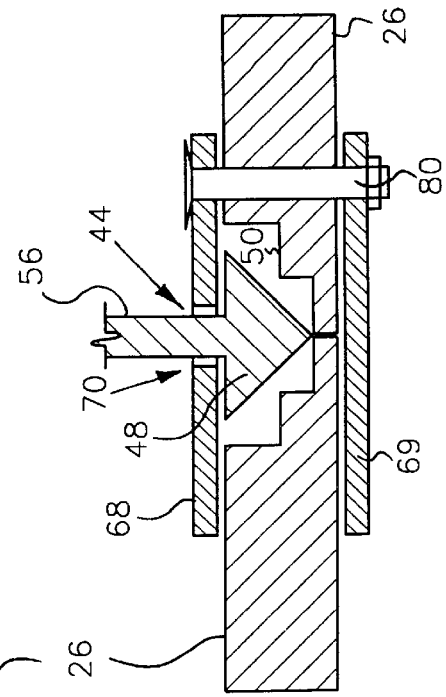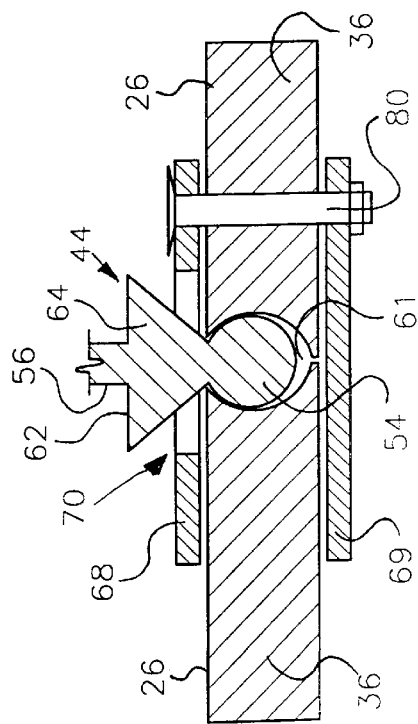

SYRINGE NEEDLE SAFETY VISE AND ASSOCIATED DISINFECTING APPARATUS

CROSS-REFERENCE TO RELATED APPLICATION

This application claims the benefit of U.S. Provisional Patent Application Serial No. 60/031,111, filed Nov. 14, 1996.

BACKGROUND OF THE INVENTION

1. Field of the Invention

The present invention relates to the field of medical safety devices, and more particularly, to a safety vise for the collection and disposal of used hypodermic needles from a reclaimable sleeve or syringe body, the safety vise having an associated disinfecting apparatus which is operably coupled to a viseing mechanism to prevent its subsequent use unless a disinfecting operation using the disinfecting apparatus has been performed, whereby disinfection of the reclaimable sleeve is encouraged. The safety vise is primarily intended for reclaiming the sleeve of a pistonless blood collection system, like VACUTAINER® assemblies, which are assembled from three independent sections: a sleeve, a specimen tube, and a double-ended needle. The design of the pistonless blood collection device requires that the safety vise have additional precautionary measures during the viseing procedure for removal of a double-ended needle.

2. Description of the Related Art

A major concern to those in the healthcare industry has been needle safety, primarily because the body of any container used in conjunction with blood handling is a potential carrier of disease and contamination. Used hypodermic syringe needles in particular are often infected with viral and bacterial pathogens which can lead to life-threatening diseases. Even as unused items, they portend a simple work-place hazard because they are extremely sharp and a skin puncture with a sterilized needle can provide an entry point for disease, especially at a medical facility.

Moreover, the problems associated with disease transmission by syringe use and disposal have imposed legal liabilities on professionals who must use them in practicing their art. Hypodermic syringe needles are prescribed medical items and desirable in drug trafficking. Therefore, to enforce regular prevention programs encouraging health and safety, medical facilities must execute prophylactic protocols or incur liabilities as dictated by law and regulation. One adopted protocol entails removing hypodermic syringe needles by a one handed technique to prevent inadvertent needle sticks.

However, used blood collection assemblies of a particular type using double-ended needles pose unique problems which have heretofore gone largely unaddressed. Referred to herein generally as a "pistonless blood collection system" and exemplified by the VACUTAINER® syringe and similar assemblies, these systems are well known and commonly used throughout the medical industry. To appreciate the problems such a system poses, an understanding of its components and its use is necessary.

A pistonless blood collection system is characterized generally as a pistonless, evacuated syringe for the collection of blood samples. The system consists of three separable components: 1) a blood specimen tube which is evacuated to a pressure below atmospheric and sealed with a rubber stopper; 2) a sleeve comprising a short transparent plastic cylinder accommodating both the rubber stopper and the specimen tube in a sliding fit within the chamber of the cylinder; and 3) a double-ended hypodermic needle, having an upper needle end designed to axially penetrate the rubber stopper, a lower needle end for insertion into a patient, and a threaded hub disposed around the needle intermediate the upper end and the lower end. The sleeve has an open end, into which the tube is inserted, and a closed end. The open end of the sleeve has flanges for grasping the cylinder between the index finger and middle finger. The closed end possesses a female threaded nozzle providing a passage into the chamber of the cylinder and shaped to accept the threaded hub of the double-ended hypodermic needle. The hub of the double-ended needle is matingly adapted to screw into the nozzle of the sleeve whereby the upper end of the needle resides wholly within the chamber. Details of such an assembly, may be viewed in FIG. 11 herein and are discussed further in the detailed description below.

In using the pistonless blood collection system, the double-ended needle is snugly screwed into the nozzle of the sleeve, forming an unitary syringe body. Thereupon, the specimen tube container is slipped, stoppered-end first, into the open end of the sleeve, being sure to avoid penetration of the rubber stopper by the upper needle end. The assembly is now ready for use. The operator grasps the cylinder of the sleeve in one hand (selectively between either, the index finger and thumb and the middle finger, or, the index finger and the thumb) below the flanges and penetrates the skin of the patient with the lower needle end. Having found the vein, the operator uses his thumb to press the specimen tube so that it slides forward within the chamber so that the upper needle end penetrates the center of the rubber stopper. A flow of blood results because of the differential pressure through the needle from the chosen vein of the patient into the specimen tube. After an adequate blood sample is obtained, the assembled syringe system is withdrawn from the patient.

The pistonless blood collection system is then disassembled. The filled specimen tube is stored for routing to the laboratory. The double-ended needle must be disposed as required. However, the plastic sleeve is salvaged for reuse by disinfecting it. Occasionally, in removing the specimen tube from the sleeve, blood residing in the upper needle is ejected into the plastic sleeve, resulting in contamination. Moreover, in removing the needle for disposal, even if the lower end is removed without incident by conventional means, the upper needle remains an exposed threat.

Thus, the use of a pistonless blood collection system poses two disease-transmission concerns. First, a concern exists over the potential for cross-contamination arising from the reuse of the sleeve. Specifically, a potential exists for spreading diseases by drawing infected blood from patients and passing it through the sleeve to subsequent patients requiring a blood draw. The second concern is the obvious threat posed by an exposed, potentially contaminated, double-ended needles.

No other invention is known to encourage the cleaning of the inside of the sleeve of a pistonless blood collection system before reuse. At best, the syringe bodies are currently soaked in a disinfectant or bleach on a random and unsystematic basis. Moreover, no other inventions mechanically couple a viseing mechanism with a disinfecting means.

The following U.S. patents are only generally relevant to the invention in so far as various means to accommodate removal and disposal of needles by a one-handed technique is described. Most notably, U.S. Pat. No. 4,989,307 to Sharpe et al. describes a phlebotomy syringe needle hub rotating mechanism which removes the double-ended needle for storage in a disposable needle enclosure. Although the use of only one hand is necessary to insert the syringe, the apparatus fails to provide means for adequate protection against an upper needle stick by the double-ended needle. Nor is the apparatus mechanically coupled with a disinfecting unit.

U.S. Pat. No. 4,380,292 to Cramer describes a parenteral needle receptacle, namely a foam block and case, which allows health care providers to temporarily dispose of a needle quickly and safely while only using one hand by inserting the needle into the foam block. U.S. Pat. No. 5,368,576 to Brown et al. describes a housing using a curable epoxy to permanently bind a needle penetrated into the housing. In U.S. Pat. No. 4,938,514 to D'Addezio, a needle cap holder, similar in appearance to a clothespin, is used to extend a needle cap away from the grasping hand to prevent needle sticks. U.S. Pat. No. 5,383,862 to Berndt et al. describes a device for enveloping and disinfecting sharp instruments comprising a folded pad-like sheet material to which an outer protective layer is attached and having microcapusules containing a disinfectant. Another device to laterally receive needles is a disposable, frictional gripper shown in U.S. Pat. No. 5,472,433 to Suzuki.

Other disinfecting devices are also relevant to the general concept of preventing the spread of disease by contact with blood. U.S. Pat. No. 5,427,234 to Upchurch describes a method and device for disposing syringes wherein a disposable container of a height less than that of a syringe needle contains an anti-microbic fluid into which the syringe needle is inserted. The fluid is repeatedly drawn into the syringe to ensure disinfection of the syringe and needle before the entire assembly is disposed. U.S. Pat. No. 5,168,612 to Schultz et al. describes a complex shearing machine for destroying and disinfecting hypodermic needles and syringes. U.S. Pat. No. 5,212,362 to Burden et al. describes an electrical apparatus using an electrode to create an electrical arc which volatilizes a sharp instrument.

For sake of full disclosure, the following patents are noted. WIPO Pat. Application 89/03987 dated May 5, 1989 describes an apparatus for quality control for manufacture of hypodermic needles. German Offenlegunsschrift 3 842 107 dated Jun. 21, 1990 describes a guard sheath first slipped over a syringe barrel and then unidirectionally and telescopically slid over the needle from the barrel.

None of the above inventions and patents, taken either singularly or in combination, describe the instant invention as claimed. Thus, the present invention is described which permits removal of a used needle from a pistonless blood collection syringe body or other syringe, and encourages disinfection of a syringe body to eradicate potential contamination on a salvaged syringe component. The present invention provides a solution to the aforementioned problems associated with the potential transmission of disease by improper handling of needles and syringe bodies.

SUMMARY OF THE INVENTION

The present invention relates to a hypodermic syringe needle vise for collection and disposal of used hypodermic needles and an associated disinfecting apparatus which may be operably coupled to the vise to prevent subsequent operation of the vise unless a disinfecting operation using the disinfecting apparatus is performed. Although the safety vise according to the present invention is primarily intended for use with pistonless blood collection systems like VACUTAINER® assemblies or similar systems, wherein a double-ended needle requires additional precautionary measures during the viseing procedure and disinfection of a reclaimable sleeve is encouraged, it should be understood that it is equally suited for removal and cleaning of other syringe assemblies.

The prior art of the VACUTAINER® assemblies or similar systems is a body fluid specimen collection system assembled from three independent sections: a plastic sleeve, a specimen tube, and a double-ended needle. The present invention is used to safely disassemble the needle from the plastic sleeve and to disinfect the sleeve so it may more safely be reused.

The preferred embodiment of the present invention includes several interactive components. A disposable, needle collection container having an open top is provided for collection of used needles and as a base for seating a project top. The project top includes a housing having a first station and a second station. The first station of the housing is for removing a hypodermic needle from a syringe body, and has guard elements particularly structured for safely removing the double-ended needle from the sleeve of a pistonless blood collection system. The second station of the housing is for disinfecting the sleeve (or syringe body). Further, the housing defines an aperture in communication with the interior of the project top in both stations. A viseing mechanism is internally affixed to the housing of the project top and operably links the first station to the second station so that, after a needle and syringe is initially introduced into the first station and the viseing mechanism is used to remove the needle in a one handed technique, the viseing mechanism is rendered subsequently inoperable unless the needle is disengaged from the viseing mechanism by operation of disinfecting the sleeve at the second station.

In the preferred embodiment of the project top, the viseing mechanism comprises a pair of elongated jaw members having a first end and a second end, each jaw member positioned generally parallel to one another on opposing sides of a pivot means, for example a post possibly depending from the housing about which the jaw members rotate. The pivot means are eccentrically positioned nearest the first end of the jaw members thereby defining a short portion and a long portion of each jaw member. A compressed spring or other biasing means is disposed between the first end of each jaw member to bias each jaw member against the another, thereby causing a pinching action at the second end of the viseing mechanism. The jaws of the jaw members are located on the long portion proximate to the pivot means and distal from the second end allowing a wedge to be driven between the long portion of the jaw members proximate to the second end in order to separate the jaws. Initially however, when a needle hub is inserted into the jaws of the jaw members, the biasing means provides sufficient pressive force to hold the needle hub in the grip of the jaw members, allowing the user to twist the needle hub off of the sleeve by a conventional one handed technique.

The second station includes a disinfecting component for introduction of a contaminated sleeve, to which a plying component is attached. The plying component separates the jaw members and disengages the needle from the grip of the viseing mechanism when the disinfecting operation is commenced, allowing the needle to drop into the collection container by force of gravity.

The disinfecting component of the preferred embodiment includes a cup and wicking sponge protruding from the cup, each dimensioned to closely pass into the chamber of the sleeve so as to thoroughly bring disinfectant solution contained within the cup into contact with the internal walls of the sleeve during a swabbing action. An alternative embodiment provides just a cup containing disinfectant solution, into which the nozzle of the sleeve is pressed allowing the solution to flow into and fill the chamber of the sleeve. Such an alternative cup may be provided with a wiping means which dries the outside of the sleeve as it is being removed.

The plying component may be variously functionally designed in combination with the viseing mechanism. In the preferred version, the plying component operates on a plunger principle being the action where, when the sleeve is pressed downwardly into the disinfecting component, a wedge attached to the disinfecting component is driven between the jaw members to separate the jaws. The wedge is preferably presented in a downward direction perpendicular to a horizontal direction of separation of the jaws, thereby allowing the needle to drop by force of gravity into the collection container. In an alternative embodiment, the plying component is a cam engaged between the jaw members such that, as the cam is rotated, the bulge of the cam separates the jaw members. Applied torque is transferred from the cup as it rotates while the sleeve is swabbed in a rotational motion.

Other desirable features and components may include a disinfecting solution stored in the bottom of the disposable needle collection container, and, a separate base for mating a disposable collection container to a work bench, the base having individual disinfecting components (not coupled to the viseing mechanism) and drying posts fixed to the base. Alternatively, individual disinfecting components and drying posts can stand independently to be used with any other needle removal system.

Finally, to prevent the threat of a needle stick by a double-ended needle, each station is provided with guarding means. A first means is a cylindrical wall having a height from the surface of the first station to prevent contact with the tip of upper needle while gripped in the viseing mechanism. A second means provides a configuration in which the viseing mechanism is positioned below the upper surface of the housing such that a removed needle resides entirely within the confines of the interior of the project top housing.

The present invention fosters disinfecting protocol of the sleeve after every use for later reuse. When the needle collection container is full, the project top is covered and the needle collection container and the project top are disposed of in the proper and lawful manner.

Accordingly, it is a principal object of the invention to provide a means to safely remove a used needle from a reusable component and disinfect the reusable component.

It is another object of the invention to comply with statutory and procedural protocol for the handling and disposal of syringe components.

It is a further objective of the invention to provide a means which encourages the cleaning of reusable components associated with a pistonless blood collection system.

Still another object of the invention is to provide a simple, safe, economical and compact work station for the handling, disposal, disinfecting and storage of syringe components.

It is an objective of the invention to provide improved elements and arrangements thereof in a hypodermic needle remover and disinfectant or bleach cleaner for the purposes described which is inexpensive, dependable and fully effective in accomplishing its intended purposes.

These and other objectives of the present invention will become readily apparent upon further review of the following specification and drawings.

BRIEF DESCRIPTION OF THE DRAWINGS

FIG. 4, FIG. 5, and FIG. 6 are diagrammatic, sectional side views of a fourth embodiment, the second embodiment and the first embodiment, respectively, of the safety vise according to the present invention.

FIG. 7, FIG. 8, and FIG. 9 are diagrammatic, cross sectional views of three different embodiments of a wedge component of the safety vise, as may be alternatively taken along section line 7,8,9—7,8,9 as shown in FIG. 1.

Similar reference characters denote corresponding features consistently throughout the attached drawings.

DETAILED DESCRIPTION OF THE PREFERRED EMBODIMENTS

The present invention relates to the field of medical safety devices, and more particularly, to a safety vise for the collection and disposal of used hypodermic needles from a reclaimable sleeve or syringe body. The safety vise has an associated disinfecting apparatus which is operably coupled to a viseing mechanism to prevent subsequent use of the apparatus unless a disinfecting operation using the disinfecting apparatus is performed, whereby disinfection of the reclaimable sleeve is encouraged.

Figure 11:
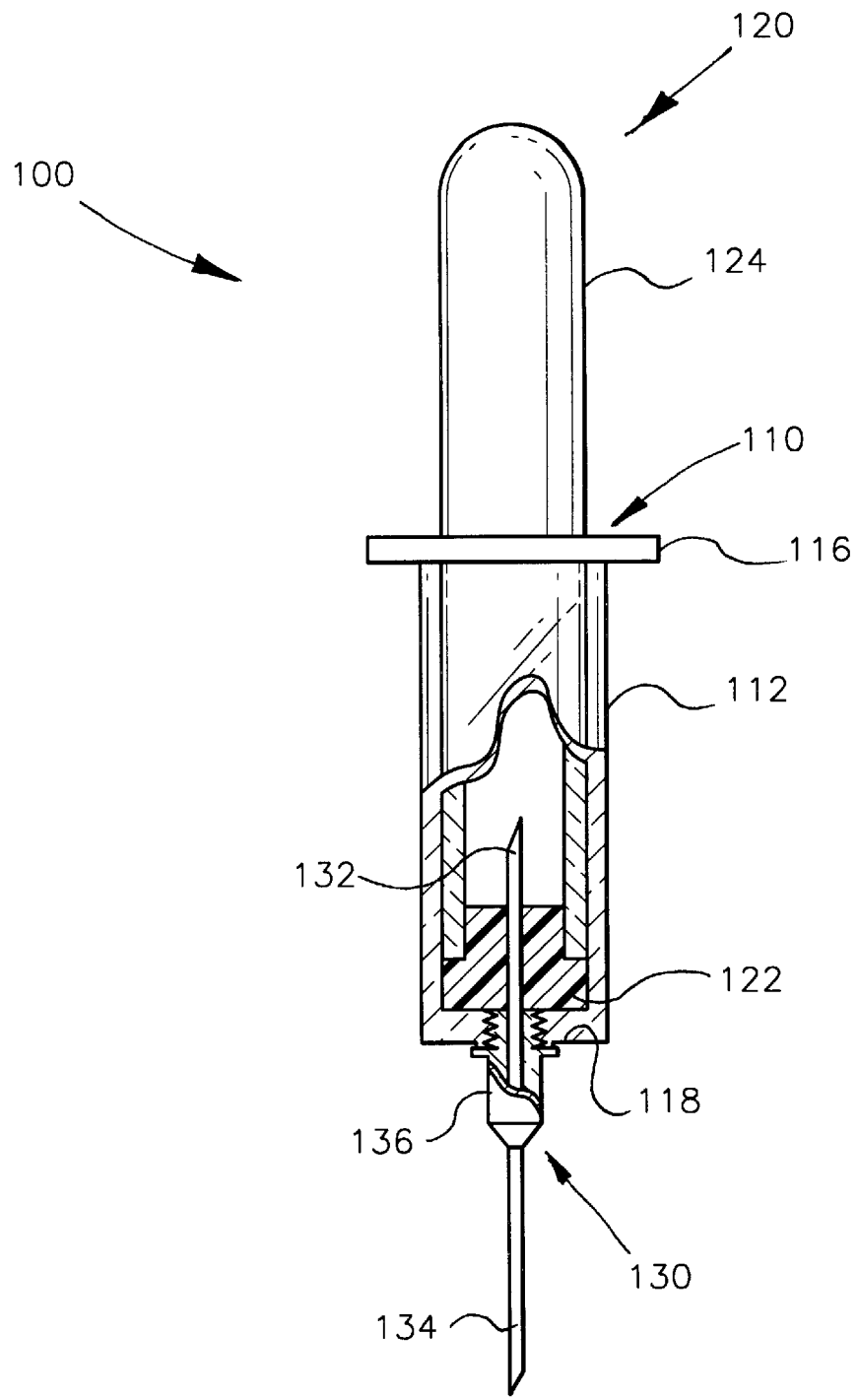
FIG. 11 is a partially fragmented, elevational view of a pistonless blood collection system as known in the prior art.

Referring first to the prior art as shown FIG. 11, a pistonless blood collection system 100, like a VACUTAINER® assembly, is shown for better appreciation of the present invention. The pistonless blood collection system 100 is assembled from three independent sections: a sleeve 110, a specimen tube 120, and a double-ended needle 130. The specimen tube 120 comprises a glass tube 124 and a rubber stopper 122. The sleeve 110 includes a short transparent plastic cylinder 112 terminating in an annular flange 116. The sleeve has an open end proximate to the flange 116, into which the specimen tube 120 is inserted, and a closed end with female threaded nozzle 118 providing a passage into the chamber of the cylinder 112. The double-ended hypodermic needle 130 has an upper needle end 132 designed to axially penetrate the rubber stopper 122, a lower needle end 134 for insertion into a patient, and a threaded hub 136 attached intermediate of the upper and lower needle ends. The hub 136 is matingly threaded to screw into the female threaded nozzle 118 such that the upper needle 132 resides wholly within the chamber of the cylinder 112.

The sleeve 110 accommodates the rubber stopper 122 and the glass tube 124 in a sliding fit within the chamber of the cylinder 112. The specimen tube 120, normally evacuated to a pressure below atmospheric and sealed with the rubber stopper 122, is shown in FIG. 11 as fully inserted into sleeve 110 such that the needle 130 penetrates the rubber stopper 122 as would be the state of the system 100 during blood draw.

Referring now to the Figures together, the safety vise 10 is shown partially fragmented to show a functional internal design (FIG. 1) and an external appearance of a different embodiment (FIG. 2) of the present invention. Although multiple embodiments are suggested by the Figures, the preferred embodiment of the present invention includes several essential interactive components.

Figure 1:
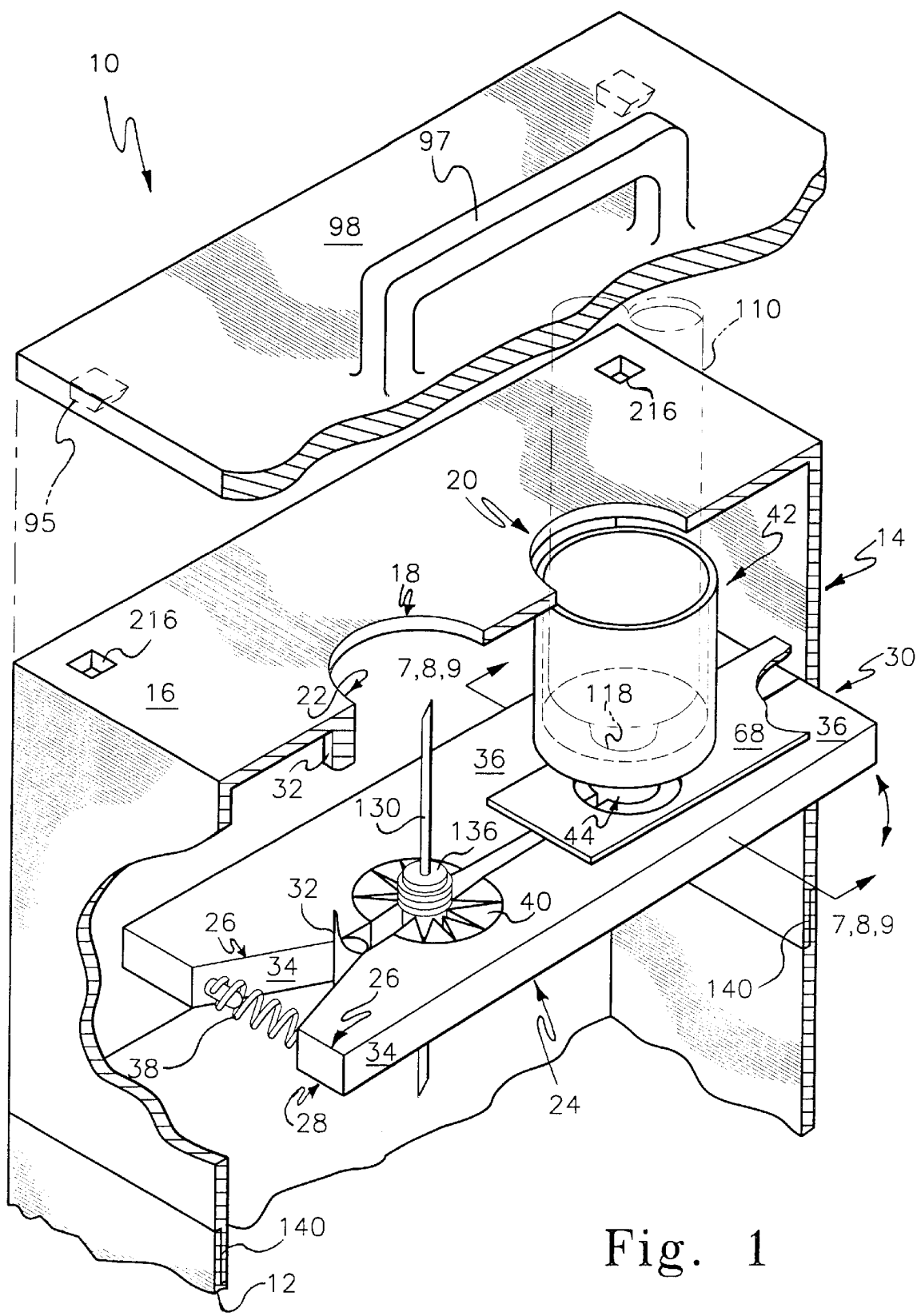
FIG. 1 is a fragmented, environmental perspective view of a first embodiment of the safety vise according to the present invention, diagrammatically representing the critical operating features.
Figure 2:
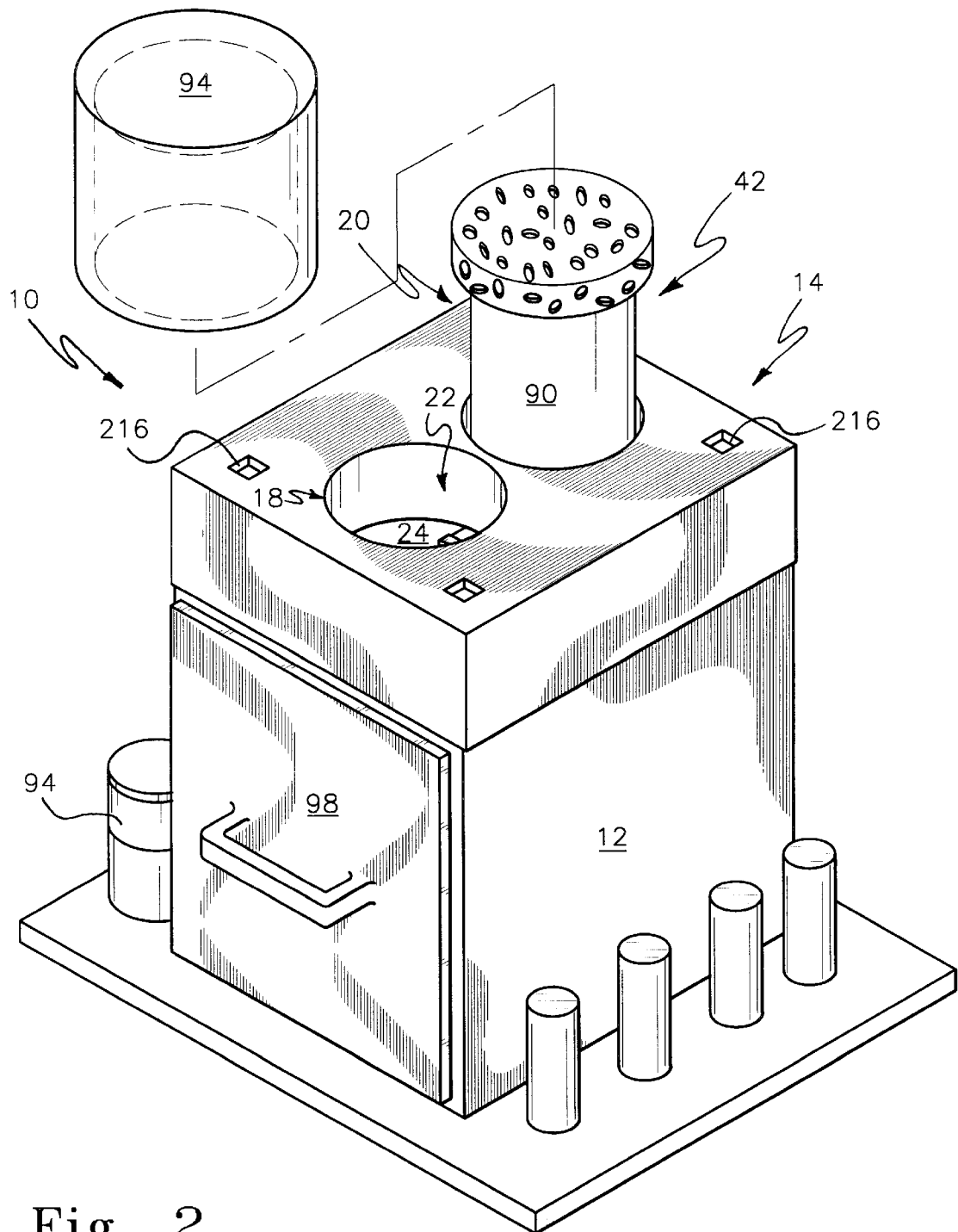
FIG. 2 is an external, perspective view of a second embodiment of the safety vise according to the present invention.

First, as best appreciated from FIGS. 1 and 2, a disposable, needle collection container 12 having an open top is provided for collection of used needles and as a base for seating a project top 14. The project top 14 includes a housing 16 having a first station 18 for removing a hypodermic needle from a syringe body, and a second station 20 for disinfecting a sleeve 110.

Next, a viseing mechanism 24 is internally affixed to (or in alternative embodiments may in part comprise a portion of) the housing 16 of the project top 14 and operably links the first station 18 to the second station 20. As can be understood from FIG. 1, the housing 16 defines an aperture 22 in communication with the interior of the project top 14, defining in part the first station 18. This aperture 22 allows access to the viseing mechanism 24 and is of sufficient diameter to allow a needle 130 and sleeve 110 as a unit to be axially introduced into the first station 18.

By referring to each FIG. 1, 3, 7, 8, and 9, the elements of the viseing mechanism 24 and its principle of operation can be understood. In the preferred embodiment of the project top 14, the viseing mechanism 24 comprises a pair of elongated jaw members 26,26 each having a first end 28 and a second end 30. As explained below with reference to FIG. 12, one such jaw member may be selected to be formed as part of the housing during the manufacturing process, thereby reducing the number of support members, such as a pair of arms 68,69 which otherwise depend horizontally from the housing 16. In a resting state, each jaw member 26 is positioned generally parallel to one another on opposing sides of a pivot means 32, which as diagrammatically shown may be a post depending from the housing 16 about which at least one jaw rotates. The pivot means 32 is eccentrically positioned nearest the first end 28 of the jaw members 28,28 thereby defining a short portion 34 and a long portion 36 of each jaw member 28. A biasing means, such as a compressed spring 38, is disposed between the short portion 34 of each jaw member 26 to bias each jaw member 26 against the another, thereby causing a pinching action at the second end 30 of the viseing mechanism 24. The jaws 40 of the jaw members 26 are located on the long portion 36 proximate to the pivot post 32 and distal from the second end 30.

It is noted that, in numerous alternative embodiments which may be envisioned but are not shown herein, the pivot post may be eliminated in order to minimize the necessary parts to cause the jaw members to close about a pivot point to cause a pinching action of the long portions. For example, a suggested alternative in FIG. 12 eliminates the post by a simple arrangement simulating a common spring-biased clothespin. One of the jaw members 26a is affixed to the housing 16 at the second end 30. The other jaw member 26b is an independent piece provided with a pivot cam 33 to pivot against jaw member 26a. A coil spring 38 in the manner of a clothespin is provided to provide bias and support of the free jaw member 26b.

Figure 12:
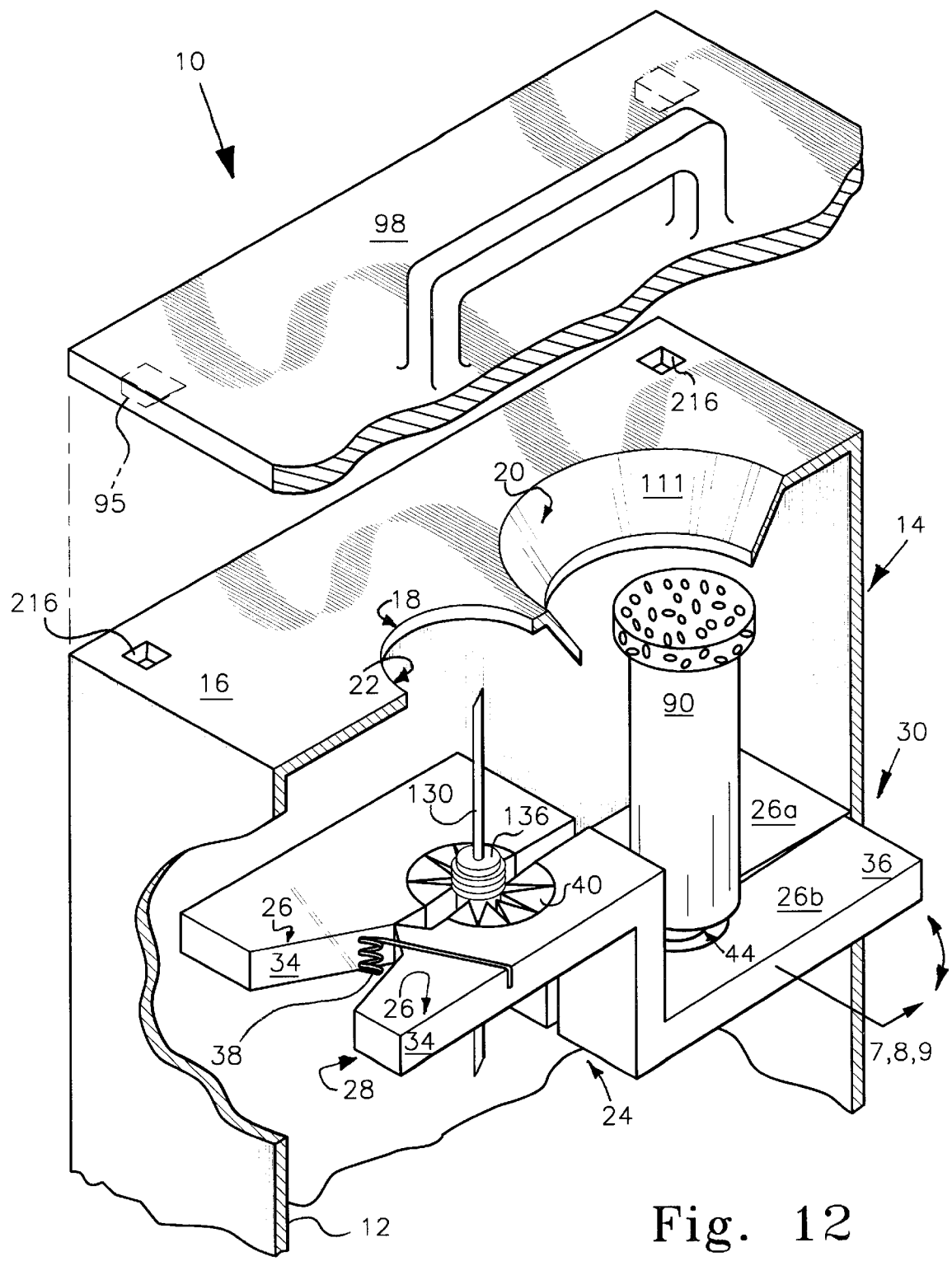
FIG. 12 is a fragmented, environmental perspective view of a fifth embodiment of the safety vise according to the present invention, diagrammatically representing the critical operating features.

Moreover, as can be readily observed from FIG. 12, both jaw members 26 may be generally Z-shaped to allow the project top 14 of housing 16 to be flat, thereby both accepting a flat lid 98 and eliminating any surface obstructions which may interfere with hygiene or cleaning protocols. The offset levels between the jaws 40 and the wedge member 44 of the swabbing post 90 are necessitated by the fact that the length of the sleeve 110 dictates the length of the swabbing post 90 which in turn is in excess of the length from the center of the hub 136 to the end of the double-ended needle 130 (by approximately one-half). Other alternative configurations may be envisioned to accommodate such offset, such as suitably angling an essentially planar viseing assembly within the project top. An annular channel 111 is also added to the housing 16 about the swabbing post 90 in order to allow a sufficient gap wherein the fingers of the user protrude while gripping the nozzle end of the sleeve 110 during the swabbing operation.

In either embodiment, but referring back to FIG. 1, when a needle hub 136 is inserted into the jaws 40 of the jaw members 26, the spring 38 provides sufficient pressive force to hold the needle hub 136 in the grip of the jaw members 26. This gripping action allows the user to twist the needle hub 136 off of the sleeve 110 by a conventional one handed technique. The sleeve 110 is then transferred to the second station 20 for disinfection; meanwhile the needle 130 remains gripped in the jaws 40. Thus, the viseing mechanism is rendered subsequently inoperable for insertion of a second needle and sleeve unit unless the prior needle 136 is disengaged from the viseing mechanism 24 by operation of disinfecting the sleeve at the second station 20.

Figure 3:
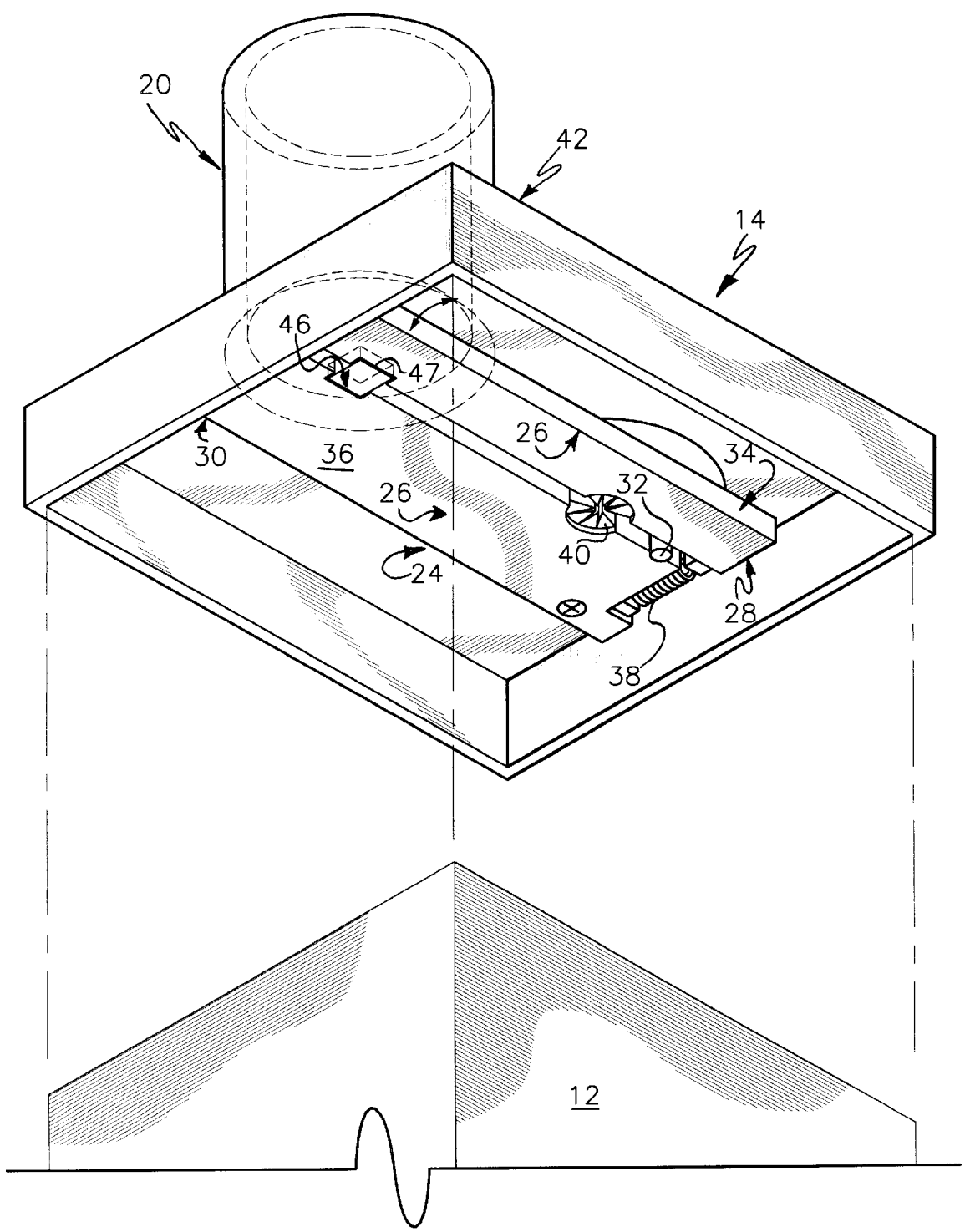
FIG. 3 is a perspective view of the underside of the project top of a third embodiment of the safety vise according to the present invention.

The second station 20 includes a disinfecting component 42 for introduction of a contaminated sleeve 110. The disinfecting component 42 is attached to an element for disengaging the needle held by the viseing mechanism 24. The disinfecting component 42 may be structured in numerous ways to be consistent with its intended function of disinfecting the sleeve 110. Various embodiments are suggested in FIG. 1, FIG. 4, FIG. 5 and FIG. 6, discussed later. Likewise, the element for disengaging the needle from the viseing mechanism 24 may also take on various embodiments consistent with its function of separating the jaw members 26. In FIG. 1, FIG. 4, FIG. 5 and FIG. 6, a schematic representation of a plying component 44 is shown attached to the disinfecting component 42. Three embodiments of the plying component 44 are shown in greater detail in FIG. 7, FIG. 8 and FIG. 9. In FIG. 3, a rotating component 46 is shown. Of course, further alternative embodiments may also be envisioned by applying the above described functional principles as exemplified by the illustrated embodiments.

Either the plying component 44 or the rotating component 46 separates the jaw members 26 and disengages the needle 130 from the grip of the viseing mechanism 24 when the disinfecting operation is commenced, allowing the needle 130 to drop into the collection container 12 by force of gravity. Whereas the plying component 44 functions as a wedge driven between the long portions 36 of the jaw members 26 proximate to the second ends 30 in order to separate the jaws 40, the rotating component 46 has a cam 47 attached to a shaft (not shown), the cam 47 engaged between the jaw members 26 such that, as the cam 47 is rotated, the bulge of the cam separates the jaw members 26 as indicated by the double-ended arrow in FIG. 3.

Referring specifically to FIGS. 7, 8, and 9, the plying component 44 may be variously functionally designed in combination with the jaw members 26. Three types of linear wedges are considered. One is a triangular driver 48 forcing open the stepped and parallel edges 50 of the long portion 36 of each of the jaw members 26 as shown in FIG. 8. A second driver 52 has a hemispherical end 54 attached to shaft 56 to force open a symmetrical split cone 60, shown in FIG. 7. The third driver 62 is a hybrid of a rounded end 54 attached to a triangular portion 64, wherein the rounded end 54 seats in a spherical recess 61 defined by the long portions 36 while positioned in a resting state, as shown in FIG. 9. The triangular portion 48 wedges between the edges of the jaw members 26, whereas the rounded end 54 prevents the wedge from being removed from second station 20 in the event that the third driver is pulled in an upward direction.

As can also be observed in FIGS. 7, 8, and 9, the jaw members 26 are supported within the project top by a pair of arms 68,69 which depend horizontally from the housing 16. The arms 68,69 are connected with one another and one of the two jaw members 26 by fastener 80, a nut and screw. The upper arm 68 of the pair 68,69 is provided with a hole 70 to allow the shaft 56 attached to the plying component 44 to pass through and connect with the disinfecting component 42 (not shown). In FIGS. 7 and 8, it can be observed the hole 70 is dimensioned to restrict the upward movement of the plying component 44, thereby preventing its removal by an upward pulling. However, as previously noted with reference to FIG. 12, manufacturing and assembly processes may dictate modifications to the preferred embodiment which may result in the presence or absence of features such as the arms 68,69.

Turning now to FIGS. 4, 5 and 6, three embodiments of the disinfecting component 42 of the present invention can seen as attached to a plying component 44 in a schematic representation. The preferred embodiment of FIG. 5 includes a cup 72 and wicking sponge 74 protruding from the cup 72 and extending beyond the diameter of the cup 72 to form a swabbing end 76. The unit is referred to as a whole as a swabbing post 90. The swabbing end 76 is dimensioned to closely pass into the chamber of the sleeve 110 so as to thoroughly bring a disinfectant solution placed within the cup into contact with the internal walls of the sleeve 110 by a wicking action as the sleeve 110 is moved in an up and down swabbing motion. As shown in FIG. 2, the swabbing post 90 may be provided with a removable cap 94 to prevent emission of odors and dehydration of the disinfecting solution and shield the swabbing post 90 while not in use. Alternative embodiments, as shown in FIG. 4 and FIG. 6, and best appreciated from FIG. 1, provide just a cup 72 containing disinfectant solution (not shown), into which the nozzle end of the sleeve 110 is pressed allowing the solution to flow through the opening in nozzle 118 and fill the chamber of the sleeve 110. A wiping means may be provided which dries the outside of the sleeve as it is being removed.

It can now be appreciated from the structure of the component parts, how the present invention operates. In the preferred embodiment, the plying component 44 operates on a plunger principle. When the sleeve 110 is pressed downwardly into the disinfecting component 42, whether swabbing post 90 or cup 72, the appropriate wedge of the plying component is simply driven between the jaw members 26 to separate the jaws 40, thereby allowing the needle to drop by force of gravity into the collection container. When the sleeve cleaning procedure is completed, and the disinfection component 44 is no longer depressed, the jaws 40 close in a passive manner, ready to engage the next needle. The passive closing of the jaws 40 is accomplished because of the jaw members 26 are acting under the force provided by the spring 38.

In an alternative embodiment, the same result is obtained when the cam 47 of rotating component 46 is rotated, by virtue of rotational forces being transmitted through shaft 56 attached to the cup 72 of swabbing post 90 during a rotational motion caused by the swabbing the sleeve 110 against the swabbing end 76.

Finally, to prevent the threat of a needle stick by a double-ended needle 130, each station 18,20 is provided with guard elements particularly structured for safely removing the double-ended needle from the sleeve of a pistonless blood collection system. As shown in FIG. 4, a first means is a cylindrical wall 94 having a height from the surface of the housing 16 to prevent contact with the tip of upper needle 132 while gripped in the viseing mechanism 24. A second means, as shown in FIG. 5, simply spaces the viseing mechanism 24 from the aperture 22 of the upper surface of the housing 16 at a distance in excess of the length of the upper needle and hub such that the tip of the upper needle resides completely within the interior of the project top 14. Moreover, a bipartite, conically-sloped guide 101 may be added annularly about the jaws 40 of jaw members 26,26 in registry with aperture 22 to direct a needle into jaws 40. Such guide 101 could function in combination with pivot post 32, wherein a bar, guide or other directional means is configured to perform both the function of the guide and the post.

When the needle collection container is full, apertures 18,20 of the project top are covered with a lid, or a suitable capping means 98, and the container is disposed of in the proper and lawful manner. As shown in FIG. 1, the capping means 98 may be a flat lid having a handle 97 on the upper surface and locking prongs 95 on the lower surface. Receiving holes 216 defined by the housing 16 are provided for receiving the locking prongs 95. The capping means 98 may be removably stored until ready for use by appropriately mating forms protruding from and attached to the collection container 12, as suggested in FIG. 2. The needle collection container 12 has a lid lip 140 (FIG. 1) to assure a hermetic seal during use, which may be permanently sealed with a cement or otherwise secured during assembly to prevent access to a contaminated container. To secure the collection container 12 to a surface, a detachable connection means 92 is attached to its bottom surface. A hook and loop fastener, magnetic strips or the like, which assure a strong adhesion of container 12 to a base, yet which allows the container 12 to be simply disconnected, is provided. Double-sided tape or other suitable securing means may also be used.

Figure 10:
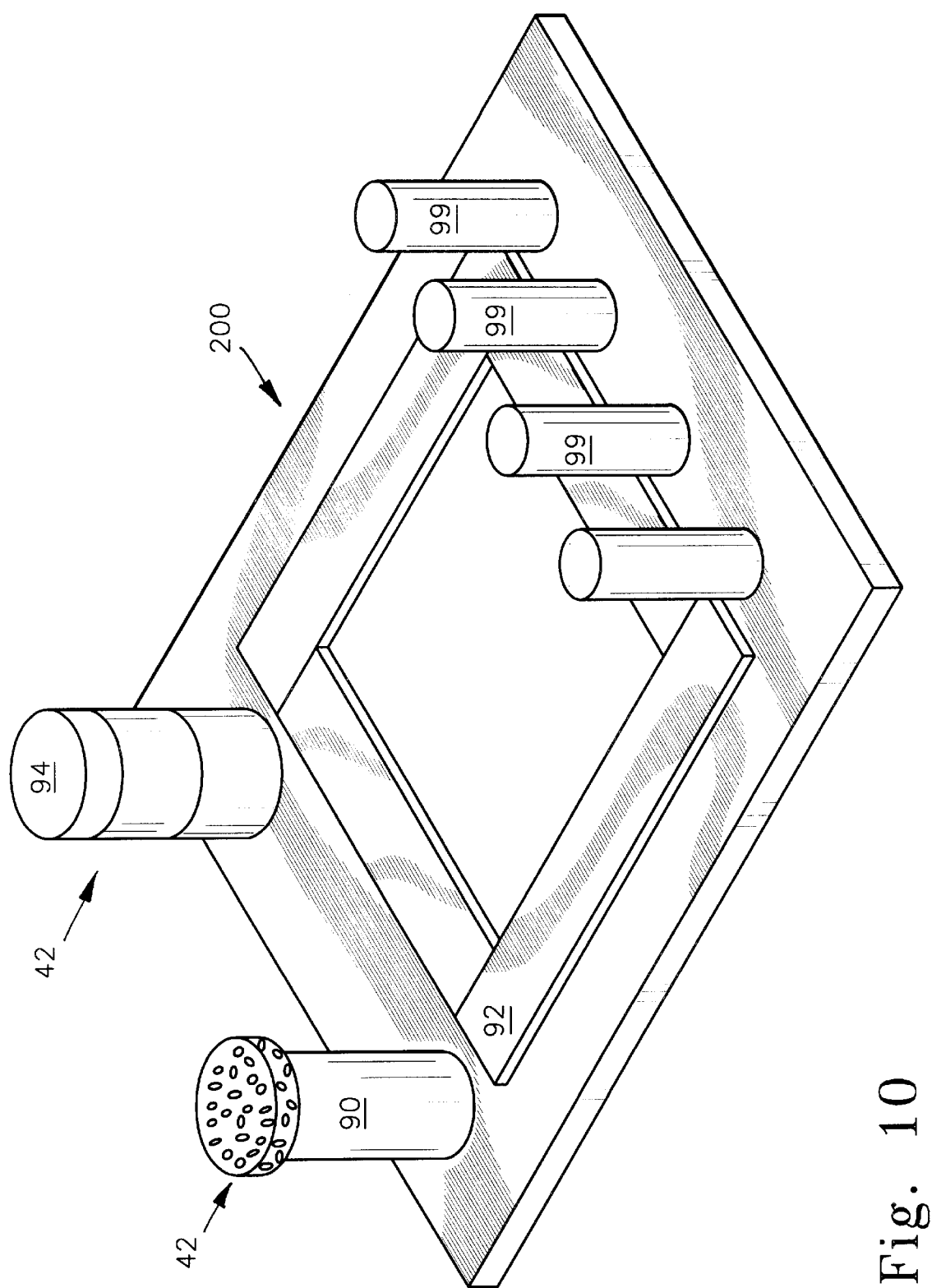
FIG. 10 is a perspective view of a base assembly for receiving a safety vise or other needle receptacle.

As illustrated in FIG. 10, the safety vise 10 may be combined with a base 200 having individual disinfecting components 42 (not coupled to the viseing mechanism), such as a swabbing post 90. The swabbing post 90 may be covered by a suitable cap 94 to prevent emission of odors and dehydration of the disinfecting solution. Drying posts 99 for holding cleaned sleeves may be fixed to the base 200. Alternatively, individual disinfecting components and drying posts can stand independently to be used with any other needle removal system which may be secured to the base by securing means 92. Moreover, the collection container 12 may include a disinfecting solution stored in the bottom of the disposable needle collection container 12.

The structures of the multiple embodiments of the project top and other components of the present invention as described in detail herein and may be variously modified by one having ordinary skill in the art; however, each embodiment relies on the same principles of operation and therefore it is to be understood that the present invention is not limited to the embodiments described above, but encompasses any and all embodiments within the scope of the following claims.

I claim:

1. A safety vise and associated disinfecting apparatus for cleaning a reclaimable syringe sleeve to which a disposable needle is removably attached, comprising:

a collection container defining an open top and a seat; and, a project top for seating on the said seat of the said open top of the collection box to form an enclosed unit, including a housing defining an aperture for axial passage of a sleeve into the enclosed unit, viseing means for releasably gripping the needle and positioned to receive the needle through the aperture, the viseing means being attached to and enclosed by the housing, a disinfecting component for containing a fluid and adapted to allow introduction of the sleeve to the fluid, and plying means for releasing the viseing means, the plying means being operably coupled to the disinfecting component such that when the disinfecting component is manipulated the viseing means are released.

2. The safety vise and associated cleaning apparatus according to claim 1, further comprising a base including a plurality of drying posts and a fastening means for securing the collection container to the base.

3. The safety vise and associated cleaning apparatus according to claim 1, wherein the viseing means include:

a pivot means;

a pair of elongated jaw members each having a first end and a second end, the pair of jaw members in a resting state being positioned generally parallel to one another on opposing sides of the pivot means, and the pivot means being eccentrically positioned nearer the first end of the jaw members, thereby defining a short portion and a long portion of each jaw member; and a biasing means disposed between the short portion of each jaw member to bias each jaw member against the another, whereby a pinching action at the second end of the viseing means is caused.

4. The safety vise and associated cleaning apparatus according to claim 3, wherein the pivot means is a post depending from the housing about which at least one jaw is rotatably attached.

5. The safety vise and associated cleaning apparatus according to claim 3, wherein the biasing means is a compressed spring.

6. The safety vise and associated cleaning apparatus according to claim 3, wherein the plying means further includes a wedge component depending from the disinfecting component, the wedge component being positioned to be driven between the long portion of the jaw members.

7. The safety vise and associated cleaning apparatus according to claim 6, wherein the wedge component is a hemispherical, rounded end, attached to a portion being triangular in cross-section, and wherein further each of the long portions of the pair of jaw members while positioned in a resting state define a spherical recess in which the hemispherical, rounded end resides.

8. The safety vise and associated cleaning apparatus according to claim 6, wherein the plying component is a cam attached to a shaft in turn attached to the disinfecting component, the cam being engaged between the jaw members such that, as the shaft of cam is rotated, the bulge of the cam separates the jaw members.

9. The safety vise and associated cleaning apparatus according to claim 1, wherein the disinfecting component is a cup having walls dimensioned and configured to closely axially receive the sleeve within its walls.

10. The safety vise and associated cleaning apparatus according to claim 1, wherein the disinfecting component is an elongated cup having walls dimensioned and configured to be closely axially introduced within the chamber of the sleeve and including a wicking sponge placed within the cup and protruding from the cup and extending beyond the diameter of the cup to form a swabbing end, wherein the swabbing end is dimensioned to closely pass into the chamber of the sleeve so as to come into contact with the internal walls of the sleeve.

11. The safety vise and associated cleaning apparatus according to claim 1, further comprising guarding means for shielding a double-ended needle while engaged in said viseing means.

12. The safety vise and associated cleaning apparatus according to claim 11, wherein the guarding means comprises a cylindrical wall disposed coaxial with the housing aperture, the cylindrical wall having a height in excess of a distance defined from the surface of the first station to a tip of the upper needle while gripped in the viseing mechanism.

13. The safety vise and associated cleaning apparatus according to claim 11, wherein the viseing mechanism is configured and positioned below the upper surface of the housing such that a removed needle resides entirely within the confines of the interior of the project top housing.

14. The safety vise and associated cleaning apparatus according to claim 1, wherein the pair of jaw members are generally Z-shaped for allowing the project top of the housing to be flat, thereby minimizing project top surface obstructions which may interfere with hygiene or cleaning protocols.

15. The safety vise and associated cleaning apparatus according to claim 1, further comprising a lid sized and configured to cover the collection container for more sanitary storage and disposal of the collection container.

* * * * *